(12) United States Patent
Huang et al.

(10) Patent No.: US 7,781,190 B2
(45) Date of Patent: Aug. 24, 2010

(54) METHOD FOR CONSTRUCTING AND MODIFYING LARGE DNA MOLECULES

(75) Inventors: Jian-Dong Huang, Hong Kong Sar (CN); Xin-Mei Zhang, Hong Kong Sar (CN); Julian Alexander Tanner, Hong Kong Sar (CN)

(73) Assignee: The University of Hong Kong, Hong Kong (CN)

( * ) Notice: Subject to any disclaimer, the term of this patent is extended or adjusted under 35 U.S.C. 154(b) by 0 days.

(21) Appl. No.: 10/892,579

(22) Filed: Jul. 16, 2004

(65) Prior Publication Data

US 2005/0084970 A1 Apr. 21, 2005

Related U.S. Application Data

(60) Provisional application No. 60/490,025, filed on Jul. 24, 2003.

(51) Int. Cl.
*C12N 15/64* (2006.01)
*C12N 15/70* (2006.01)
(52) U.S. Cl. ............ 435/91.4; 435/471; 435/488; 435/478
(58) Field of Classification Search ............... None
See application file for complete search history.

(56) References Cited

U.S. PATENT DOCUMENTS

| 6,355,412 | B1 * | 3/2002 | Stewart et al. ............ 435/4 |
| 2005/0084970 | A1 * | 4/2005 | Huang et al. ............ 435/456 |

OTHER PUBLICATIONS

Jeang, K. et al., "Organization of the Epstein-Barr Virus DNA Molecule", 1983, J. Virol., vol. 48: pp. 135-148.*
Kassavetis, G. et al., "Bacteriophage SP6-specific RNA polymerase", 1982, J. Biol. Chem., vol. 257: pp. 5779-5788.*
Brown, J. et al., "Sequences of three promoters for the bacteriophage SP6 RNA polymerase", 1986, Nuc. Acids Res., vol. 14: pp. 3521-3526.*
Narayanan, K. et al., "Efficient and precise engineering of a 200 kb beta-globin human/bacterial artificial chromosome in E. coli DH10B using an inducible homologous recombination system", 1999, Gene Therapy, vol. 6: pp. 442-447.*
Dobbins, A. et al., "Complete Genomic Sequence of the Virulent Salmonella Bacteriophage SP6", 2004, J. Bacteriol., vol. 186: pp. 1933-1944.*
Mendez, M. et al., "Functional transplant of megabase human immunoglobulin loci recapitulates human antibody response in mice", 1997, Nat. Genetics, vol. 15: pp. 146-156.*
Cohen, S. et al., "Construction of Biologically Functional Bacterial Plasmids In Vitro," Proc. Nat. Acad. Sci. USA, 1973, 3240-3244, vol. 70, No. 11.
Muyrers, J. et al., "Techniques: Recombinogenic Engineering—New Options for Cloning and Manipulating DNA," TRENDS in Biochemical Sciences, 2001, 325-331, vol. 26, No. 5.

Cohen, S. et al., "Construction of Biologically Functional Bacterial Plasmids In Vitro," Proc. Nat. Acad. Sci. USA, 1973, 3240-3244, vol. 70, No. 11.
Shizuya, H. et al., "Cloning and Stable Maintenance of 300-kilobase-pair Fragments of human DNA . . . ," Proc. Natl. Acad. Sci. USA, 1992, 8794-8797, vol. 89.
Zhang, Y. et al., "A New Logic for DNA Engineering Using Recombination in Escherichia Coli," Nature Genetics, 1998, 123-128, vol. 20.
Yu, D. et al., "An Efficient Recombination System for Chromosome Engineering in Escherichia Coli," PNAS, 2000, 5978-5983, vol. 97, No. 11.
Datsenko, K. and Wanner, B., "One-Step Inactivation of Chromosomal Genes in Escherichia Coli K-12 Using PCR Products," PNAS, 2000, 6640-6645, vol. 97, No. 12.
Muyrers, J. et al., "Point Mutation of Bacterial Artificial Chromosomes by ET Recombination," Eur. Mol. Biol. Org., 2000, 239-243, vol. 1, No. 3.
Muyrers, J. et al., "Rapid Modification of Bacterial Artificial Chromosomes by ET-Recombination," Nucleic Acids Research, 1999, 1555-1557, vol. 27, No. 6.
Liu, P. et al., "A Highly Efficient Recombineering-Based Method for Generating Conditional Knockout Mutations," Genome Research, 2003, 476-484.
Jackson, I.J. et al., "The Tyrosinase-Related Protein-1 Gene has a Structure and Promoter Sequence Very Different . . . ," Nucleic Acids Research, 1991, 3799-3804, vol. 19, No. 14.
Buchholz, F. et al., "A Simple Assay to Determine the Functionality of Cre or FLP Recombination Targets in . . . ," Nucleic Acids Research, 1996, 3118-3119, vol. 24, No. 15.
Lewandowski, M., "Conditional Control of Gene Expressiong in the Mouse," Nature Reviews, Genetics, 2001, 743-755, vol. 2.
Zhang, Y. et al., "DNA Cloning by Homologous Recombination in Escherichia Coli," Nature Biotechnology, 2000, 1314-1317, vol. 18.
Lee, E-C. et al, "A Highly Efficient Escherichia coli-Based Chromosome Engineering System Adapted for Recombinogenic Targeting . . . ," Genomics, 2001, 56-65, vol. 73.

* cited by examiner

*Primary Examiner*—Michael Burkhart
(74) *Attorney, Agent, or Firm*—Robert D. Katz; Cooper & Dunham LLP

(57) ABSTRACT

This invention provides a method for combining overlapping DNA molecules comprising: (a) providing first and second DNA fragments, the first having a region homologous to a region in the second; (b) tagging the first DNA fragment with a selectable marker; (c) cloning the first DNA sequence into a retrieval vector to form a DNA-vector complex; (d) linearizing the DNA-vector complex; and (e) inserting the first DNA fragment from the DNA-vector complex into the second DNA fragment using homologous recombination to form a combined DNA molecule; and (f) removing the selectable marker, thereby generating a combined DNA molecule. The invention further provides a vector for retrieving and inserting a selected DNA molecule into a target DNA molecule.

4 Claims, 5 Drawing Sheets

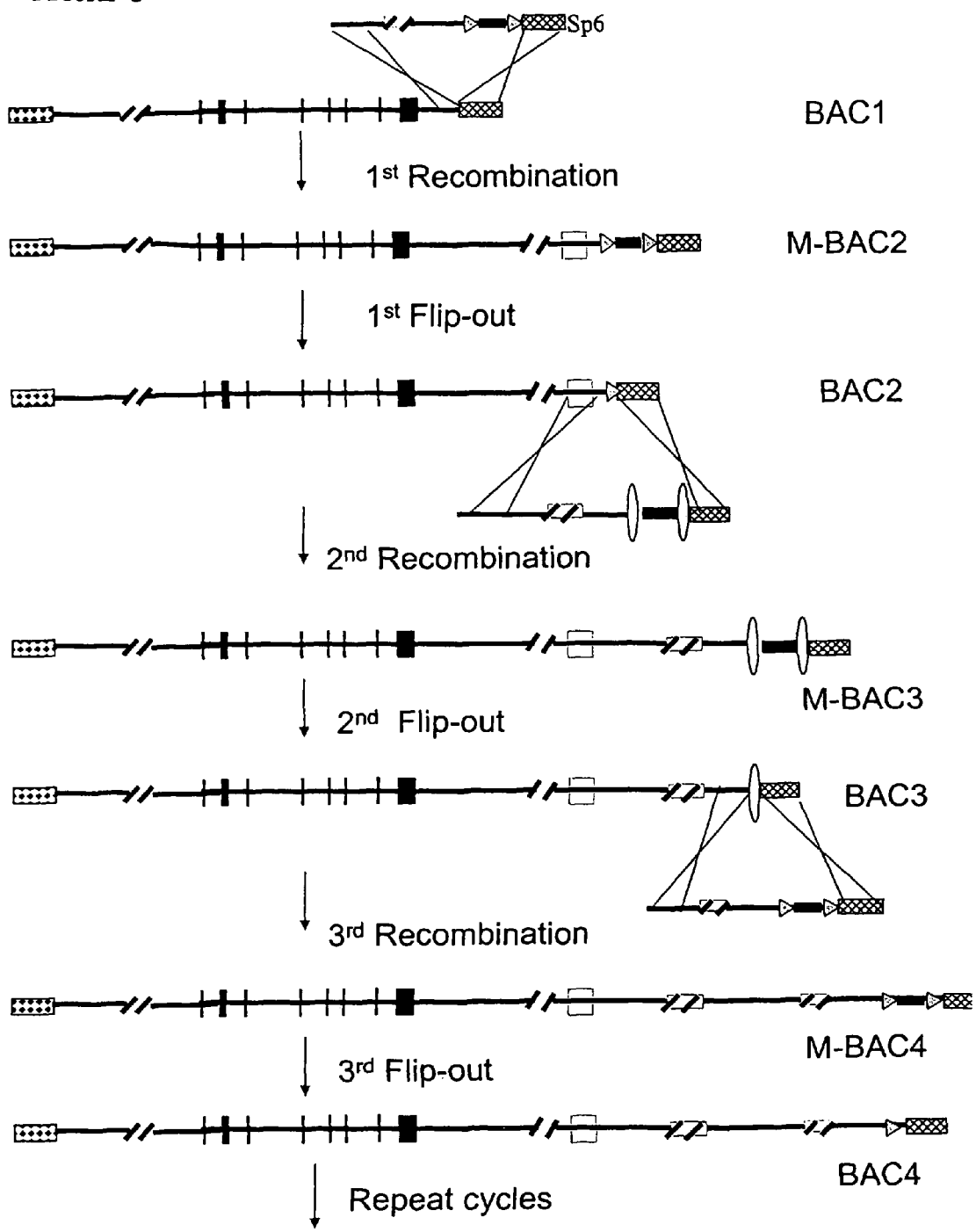

METHOD FOR CONSTRUCTING AND MODIFYING LARGE DNA MOLECULES

This application claims priority of provisional application U.S. Ser. No. 60/490,025, filed Jul. 24, 2003, the contents of which are incorporated herein by reference.

Throughout this application, various publications are referenced. Full citations for these publications may be found listed at the end of the specification immediately preceding the claims. The disclosures of these publications in their entireties are hereby incorporated by reference into this application in order to more fully describe the state of the art as of the date of the invention described and claimed herein.

BACKGROUND OF THE INVENTION

The ability to manipulate large DNA fragments is very important to contemporary biology. Although recombinant techniques were developed more than 25 years ago, improved methodologies remain highly prized, especially to aid functional genomic studies (1, 2). Conventional approaches for the manipulation of DNA are multi-step and time-consuming, involving the digestion of DNA by appropriate restriction enzymes followed by ligation into a suitable cloning vector. A critical factor in the success of traditional DNA manipulation is the length of the DNA to be engineered. Due to the demands of restriction specificity it is very difficult to manipulate DNA molecules of more than 20,000 base pairs using traditional restriction-ligation methods (3). This is of particular concern to bacterial artificial chromosome (BAC) engineering, where there is often a need to engineer DNA fragments large enough to contain the appropriate regulatory elements for a certain gene's expression (4). BACs have become powerful tools in functional genomic studies (1), so better methods for precisely manipulating BAC DNA are required.

Recently, scientists have developed a new method, known as recombineering, to manipulate large DNA fragment (5-10), and have overcome the difficulties in traditional BAC DNA engineering. These methods have been based either on the RecET proteins or the λ-recombination proteins. The RecET system is based on homologous recombination mediated by the RecE and RecT proteins. The Red system is based on homologous recombination mediated by three λ-recombination proteins, exo (α), bet (β) and gam (γ), collectively known as the Red proteins. The Red system is similar to the RecET system, but has been shown to be 50-100 times more efficient in *Escherichia coli* (6). A modified DH10B strain, called DY380, harboring a defective λ-prophage carrying the red genes under the tight control of the temperature sensitive λ-cI857 repressor has been created (10). Incubation of DY380 cells at 42° C. results in the inactivation of the temperature-sensitive λ repressor, and hence the production of the exo (α), bet (β) and gam (γ) proteins, enabling recombination. In the present study, a two-step approach based on the Red-mediated recombination was developed. In the first step, retrieval, a large DNA fragment is retrieved from a BACs. In the second step, recombination, the large DNA fragment is inserted into a second BAC to form the unified BAC containing the entire desired sequence. This task would be extremely difficult by conventional means.

SUMMARY OF THE INVENTION

This invention provides a method for combining overlapping DNA molecules comprising the steps of (a) providing first and second DNA fragments, the first having a region homologous to a region in the second; (b) cloning the first DNA sequence into a retrieval vector to form a DNA-vector complex; (c) linearizing the DNA-vector complex; and (d) inserting the first DNA fragment from the DNA-vector complex into the second DNA fragment using homologous recombination to form a combined DNA molecule.

This invention further provides a method for combining overlapping DNA molecules comprising the steps of: (a) providing first and second DNA fragments, the first having a region homologous to a region in the second; (b) tagging the first DNA fragment with a selectable marker; (c) cloning the first DNA sequence into a retrieval vector to form a DNA-vector complex; (d) linearizing the DNA-vector complex; and (e) inserting the first DNA fragment from the DNA-vector complex into the second DNA fragment using homologous recombination to form a combined DNA molecule; and (f) removing the selectable marker, thereby generating a combined DNA molecule.

This invention also provides the above methods further comprising the step of inserting the combined DNA molecule into a third DNA fragment using homologous recombination.

Finally, the invention provides a vector for retrieving and inserting a selected DNA molecule into a target DNA molecule, comprising: (a) a first DNA fragment homologous with a first region of the selected DNA molecule; (b) a second DNA fragment homologous with a second region of the selected DNA molecule; and (c) a third DNA fragment containing a rare restriction site.

Figure 1A:
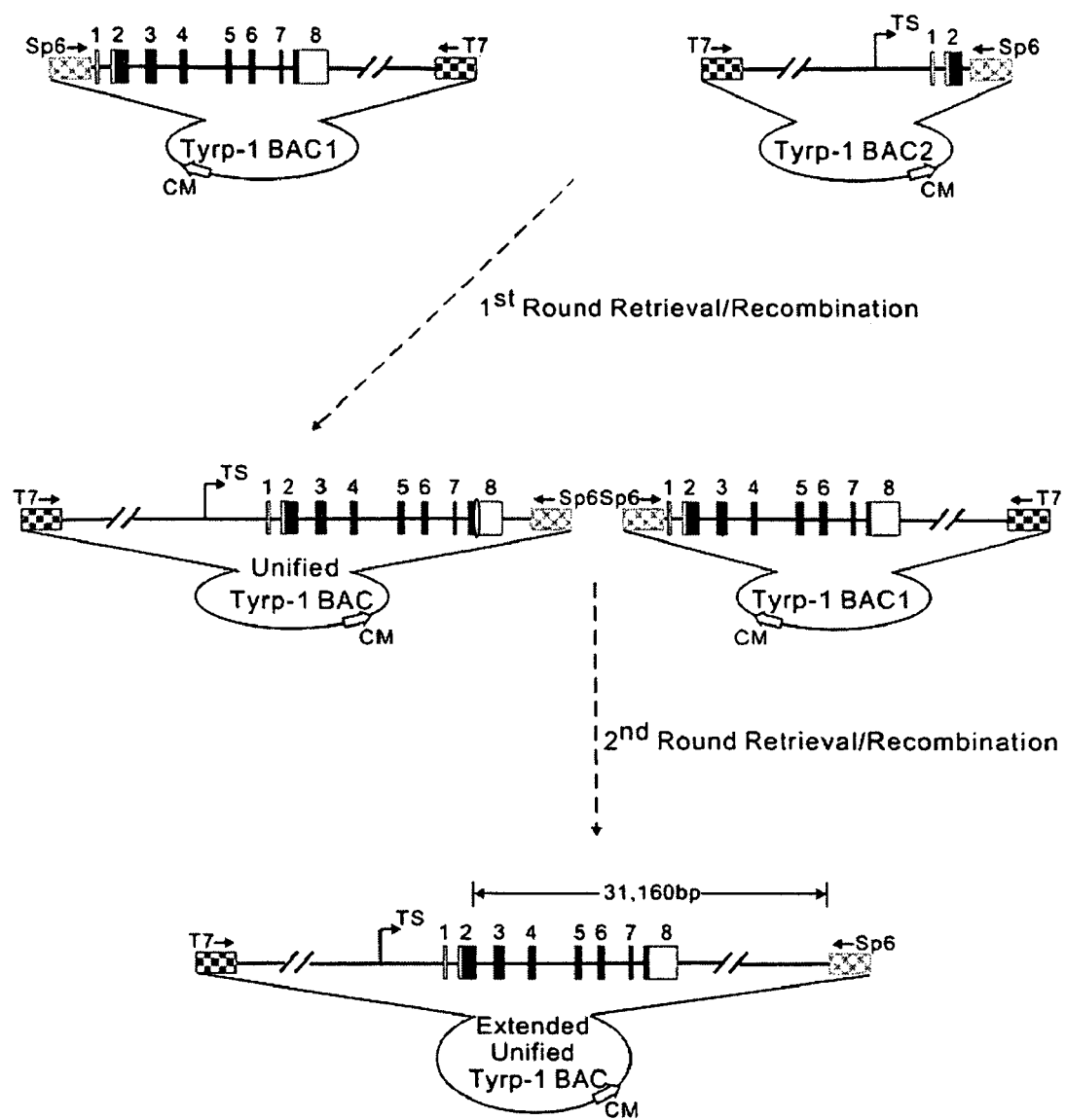
FIG. 1

General Experimental Strategy for BAC Engineering.

Hatched pattern represents the Sp6 fragment of BAC. Diamond pattern represents the T7 fragment of BAC. Vertically striped pattern represents Arm A, the breakpoint of Tyrp-1 gene of Tyrp-1 BAC1. Diagonally striped pattern represents Arm B at the end of Tyrp-1 gene of BAC1. Solid rectangles represent exons of Tyrp-1 gene. Double italic lines represent disproportional genomic DNA. Amp is Ampicillin resistance gene. Ori refers to origin of replication. Ts represents transcriptional site. ↑ represents PolyA site. ▶︎represents 3,749-bp frt-Kan$^R$-frt cassette. ▮represents frt site. ▶︎represents 1,896-bp of loxP-Kan$^R$-loxP cassette.

(A). Overall Aim of Experiment. Top left, Tyrp-1 BAC1 containing Tyrp-1 exons 1 to 8 and the 3' downstream region. Top right, Tyrp-1 BAC2 containing the Tyrp-1 5' region and exon 1 and 2. Bottom: the final extended unified Tyrp-1 BAC containing the Tyrp-1 5' region, all the exons, and a 16.5-kb 3' region. 31,160-bp is the distance between the 3' break point of Tyrp-1 BAC2 and the last base pair in the extended unified Tyrp-1 BAC.

(B). Step one: 1$^{st}$ Round Retrieval (upper left)

A kanamycin gene is first inserted into Tyrp-1 BAC1. The Tyrp-1 genomic DNA tagged by the kanamycin gene is then cloned into the retrieval vector (pBRBAC-AB). The positions of the primers which were used to amplify two homology arms are indicated by F3 & R3 and F5 & R5. In the retrieval vector, the ampicillin gene and origin of replication site are indicated by open arrows, the location of primers used to amplify the pBRBAC-AB retrieve vector are shown as thick closed arrows (R3 and F5). Homologous recombination events are denoted by crosses. NotI cleavage sites are also shown.

(C). Step two: 1$^{st}$ Round Recombination (upper right)

Linearized Tyrp-1 genomic fragment containing Tyrp-1 exon 1-8 and 4 kb 3' region was recombined with Tyrp-1 BAC2 through the homologous ArmA and Sp6 DNA regions.

The resulting Tyrp-1 BAC3 and the unified Tyrp-1 BAC contained the 5' regulatory region, all the Tyrp-1 exons and a 4 kb 3' downstream region. The position and orientation of primers (F1, R1, F2, R2, F4, F5, Sp6 and R5) that were used to detect and sequence the BACs are shown.

(D). $2^{nd}$ Round Recombination (lower)

A second round of retrieval-recombination was carried out with the unified Tyrp-1 BAC and a 19,891-bp fragment downstream of exon 8 to generate an extended unified Tyrp-1 BAC. Wave line pattern represents a long homologous arm at Tyrp-1 intron 7 upstream of the frt site in the unified Tyrp-1 BAC. The position and orientation of the primers (F6, F7, R6, and BAC-Sp6-R) that were used to detect the extended unified Tyrp-1 BAC are shown.

FIG. 2

(A). Identification of clones containing the retrieved fragment ($1^{st}$ round).

The left panel shows the digestion pattern of the retrieved BAC fragment. M: λ/HindIII DNA, Different clones labeled 1 to 6 were digested by restriction enzymes labeled above. Clones 1 to 5 show the expected digestion pattern. The right panel shows a 25.4 kb NotI-linearized pBRBAC-AB construct containing the 22.5 kb retrieved fragment.

(B). Verification of Tyrp-1 BACs with PCR.

A PCR product of 3.3 kb by primer pair (F2+R2) can only be generated after homologous recombination occurred between the retrieved DNA and Tyrp-1 BAC2 to generate Tyrp-1 BAC3 and Tyrp-1 BAC. The four figures show the PCR verification of the full length Tyrp-1 BAC3 and Tyrp-1 BAC with different primer pairs (F1+R1, F2+R2, F4+Sp6, and F5+R5). Each picture shows a band of expected size. M: 1 kb plus Marker. Template DNAs used are indicated by numbers above each lane. (1) Tyrp-1 BAC3; (2) unified Tyrp-1 BAC; (3) Tyrp-1 BAC2; (4) PCR negative control (water); (5) Tyrp-1 BAC1.

(C). Characterization of Tyrp-1 BACs by DNA fingerprint

The figure shows the DNA fingerprint results. The digestion pattern of unified Tyrp-1 BAC (labeled as 3) is very similar to that of the Tyrp-1 BAC2 (labeled as 2), but it also contains fragments unique to Tyrp-1 BAC1 (labeled as 1). The white arrows indicate DNA fragments present in unified Tyrp-1 BAC as well as in either Tyrp-1 BAC2 or Tyrp-1 BAC1, but not both. Ml: A/HindIII DNA. M2: 1 kb plus Marker. The restriction enzymes used are listed at.the top of each panel.

(D). PCR verification of $2^{nd}$ round recombination products

The two figures show the PCR verification of the second round recombination products. Two PCR products of 1.38 kb (left panel) and 6.2 kb (right-panel) by primer pair (F7+BAC-Sp6-R) and (F6+R6), respectively, can only be generated after the second round recombination has occurred between the 19,891-bp retrieved DNA and Tyrp-1 BAC, creating the extended unified Tyrp-1 BAC. Each figure shows bands of the expected size. M: 1 kb plus Marker. Template DNAs used are indicated by numbers above each lane. Lane 1: Clone 1 of extended unified Tyrp-1 BAC; Lane 2: Clone 2 of extended unified Tyrp-1 BAC; Lane 3: unified Tyrp-1 BAC.

FIG. 3

Three Rounds of Recombination

Linearized BAC1 is recombined with a DNA fragment through the homologous ArmA and Sp6 DNA regions to form BAC2. A second round of recombination is carried out with BAC2 and a downstream DNA fragment to generate an extended unified BAC3. A third round of recombination is carried out with BAC3 and a downstream DNA fragment to generate BAC4.

FIG. 4

Retrieval Vector

A, B and Sp6 fragments represent the homologous arms. Retrieval is achieved by the homologous ArmA and ArmB. Targeted recombination is performed through the homologous ArmA and Sp6 DNA regions.

DETAILED DESCRIPTION OF THE INVENTION

Definitions

As used in this application, except as otherwise expressly provided herein, each of the following terms shall have the meaning set forth below.

As used herein, homologous shall mean having the same nucleic acid sequence.

As used herein, a rare restriction site shall mean a nucleic acid sequence which occurs infrequently in the genome and is recognized by a restriction enzyme. Such rare restriction enzymes may be, but are not limited to, NotI, SmaI or SfiI.

EMBODIMENTS OF THE INVENTION

This invention provides a method for combining overlapping DNA molecules comprising the steps of (a) providing first and second DNA fragments, the first having a region homologous to a region in the second; (b) cloning the first DNA sequence into a retrieval vector to form a DNA-vector complex; (c) linearizing the DNA-vector complex; and (d) inserting the first DNA fragment from the DNA-vector complex into the second DNA fragment using homologous recombination to form a combined DNA molecule.

In one embodiment, the DNA fragments are genomic DNAs or cDNAs. In another embodiment, the DNA fragments comprise at least 20 kb. The DNA fragments may comprise bacterial artificial chromosomes (BACs), mouse artificial chromosomes (MACs) or human artificial chromosomes (HACs).

In a further embodiment, the retrieval vector comprises an Sp6 or other fragments homologous to the target vectors. In another embodiment, the homologous recombination is Red-mediated homologous recombination.

The above method may further comprise the step of inserting the combined DNA molecule into a third DNA fragment using homologous recombination.

This invention further provides a method for combining overlapping DNA molecules comprising the steps of: (a) providing first and second DNA fragments, the first having a region homologous to a region in the second; (b) tagging the first DNA fragment with a selectable marker; (c) cloning the first DNA sequence into a retrieval vector to form a DNA-vector complex; (d) linearizing the DNA-vector complex; and (e) inserting the first DNA fragment from the DNA-vector complex into the second DNA fragment using homologous recombination to form a combined DNA molecule; and (f) removing the selectable marker, thereby generating a combined DNA molecule.

In one embodiment, the DNA fragments are genomic DNAs or cDNAs. In another embodiment, the DNA fragments comprise at least 20 kb. The DNA fragments may comprise bacterial artificial chromosomes (BACs), mouse artificial chromosomes (MACs) or human artificial chromosomes (HACs).

In a further embodiment, the retrieval vector comprises an Sp6 fragment. In another embodiment, the homologous recombination is Red-mediated homologous recombination.

The above method may further comprise the step of inserting the combined DNA molecule into a third DNA fragment using homologous recombination.

Finally, the invention provides a vector for retrieving and inserting a selected DNA molecule into a target DNA molecule, comprising: (a) a first DNA fragment homologous with a first region of the selected DNA molecule; (b) a second DNA fragment homologous with a second region of the selected DNA molecule; and (c) a third DNA fragment containing a rare restriction site.

The following experimental details are intended to be exemplary of the practice of the present invention, and should not be construed to limit the scope of the invention in anyway.

EXPERIMENTAL DETAILS

Synopsis

Recombinogenic engineering or recombineering is a powerful new method to engineer DNA without the need for restriction enzymes or ligases. Described below is a general method of using recombineering to combine overlapping bacterial artificial chromosomes (BACs) to built larger, unified BACs. In order to test the feasibility of using recombineering to combine two large DNA fragments (>20 kb), a unified BAC was constructed containing the full-length Tyrosinase-related protein-1 gene (Tyrp-1) from two library derived BACs, one containing the 5' regulatory elements, and the other containing the 3' coding exons. This was achieved using a two-step homologous recombination method enabled by the bacteriophage lambda Red proteins. In the first step, retrieval, a large DNA fragment (~22 kb) was retrieved from one of the original BACs. In the second step, recombination, the retrieved DNA fragment was inserted into the second original BAC to form the unified BAC containing all the desired Tyrp-1 sequence. To further demonstrate the general applicability of this approach, an additional DNA fragment (~20 kb) was inserted into the unified BAC downstream of the coding region. This method should prove very useful for enabling BAC manipulation in a variety of scenarios.

Materials and Methods

Enzymes, Media and Bacterial Strains

Restriction enzymes were purchased from New England Biolabs unless indicated otherwise. T4 DNA ligase was from Gibco. Chloramphenicol (Cm), Kanamycin (Kan) and Ampicillin (Amp) were from Sigma. *E. coli* transformants were selected on tryptone-yeast extract agar medium containing the appropriate antibiotic at 12.5, 15 and 50 µg/ml, respectively. Primers were from Gensetoligo (Singapore). Plasmids were purified using a Qia Prep mini-prep kit (QIAGEN). PCR products and restriction enzyme digest products were recovered with GeneElut™ Agarose spin columns (Sigma). The genotype of DY380 (a gift from D. Court) is DH10B [λcI857 (cro-bioA) <>tet] that means it harbors a defective λ-prophage carrying the red genes, but tet replaces the segment between cro and bioA in DY380 strain. The genotype of 294-Flp was generated by integrating 705-Flp into the lacZ locus of *E. coli* strain, MM294 (12) (a gift from AF Stewart).

Construction of plasmids

Two adjacent DNA fragments (70bp and 500bp) from the 3' portion of Tyrp-1 BAC1 were amplified by PCR and cloned into the SalI and SacI sites of the pIGCN21 plasmid containing a frt-Kan$^R$-frt cassette (10) to generate the pIGCN21-Tyrp1 plasmid. The 70bp-and-500bp-flanked frt-Kan$^R$-frt cassette was then amplified from the pIGCN21-Tyrp1 plasmid with PCR primers (5'TTTGTCGACGCTGTTC-GAAGCCTTCACAACC-3' (SEQ ID NO:1) and 5'-TTTGAGCTCCATGTGTGGCAAGGACTGTGAC-3') (SEQ ID NO:2) and used to tag the Tyrp-1BAC1.

The pBRBAC was constructed by subcloning a 870-bp EcoR I -digested fragment from pBeloBAC11 (4) into the EcoR I-site of pBR322. The pBRBAC-AB retrieval vector was generated by inserting a 216-bp NdeI/EcoRV- homologous fragment (termed ArmA) and a 330-bp EcoRV/SacI-digested homologous fragment (termed ArmB) into the NdeI/SacI sites of pBRBAC. ArmA and ArmB were PCR amplified from Tyrp-1 BAC1 with primers F3: 5'-TTCATATG-GCAAAATCTCTTCAGCGTC-3' (SEQ ID NO:3) (italics indicating the NdeI site), R3: 5'-TTGATATCGAA-GAGATTTTCTGCCAGAC-3' (SEQ ID NO:4) (italics indicating the EcoRV site), F5: 5'-TGATATCTCATTTCATGC-CAGTGCCAC-3' (SEQ ID NO:5) (italics indicating the EcoRV site), and R5: 5'-GAGCTCAGAACAAATAAAACC-3' (SEQ ID NO:6) (italics indicating the SacI site). The ArmA-Amp-Ori-Sp6-ArmB targeting cassette used for retrieving the 22.5kb of Tyrp-1 gene was amplified from pBRBAC-AB retrieval vector with primers R3 & F5 (see above). PCR products were purified using a QIA quick PCR Purification Kit (QIAGEN) and digested with DpnI to remove DNA template. The linearized ArmA-Tyrp-1-ArmB-Sp6targeting cassette used for targeting into the 5' end of Tyrp-1 gene in Tyrp-1 BAC2 was generated by digestion with NotI.

Preparation of the Competent Cells DY380 and Generation of Recombinants

For BAC modification, DY380 were transformed with Tyrp-1 BAC1 and Tyrp-1 BAC2 separately. A single colony was cultured in LB (+Cm) at 32° C. for 16 hours, then diluted 50-fold in LB medium (+Cm) and grown to an $OD_{600}$=0.5-0.7. 10 ml cultures were exposed to 42° C. for 15 minutes to induce recombination activity, then chilled on ice for 20 min. Cells were then centrifuged for 8 minutes, 5,500 g, at 4° C. and washed with 1 ml ice-cold sterile 10% glycerol for three times. Cells were resuspended in 80 µl ice-cold sterile 10% glycerol containing 100 ng linear DNA and electroporated. One ml of LB-media was added after electroporation. Cells were incubated at 32° C. for 1.5 hours with shaking then spread on appropriate selective agar media.

PCR and Sequence analysis

BAC DNAs were purified with QIAGEN$^R$ Plasmid Purification Maxi kits. Tyrp-1 BAC was sequenced using an ABI 310Sequencer with primers (F1, R1, F2, R2, F4, F5, R5 and Sp6) to confirm the position and orientation of the 22.5kb fragment inserted into Tyrp-1 BAC2. Primers were F1: 5'-TCTAGACTTTTCTGTTTAATGTT-3' (SEQ ID NO:7), R1: 5'-TAAGTAGGCTTCAGTGACTAGATTC-3' (SEQ ID NO:8), F2: 5'-GCCTCACGATAACAATTCCCTCTAC-3' (SEQ ID NO:9), R2: 5'-GGCCAATGTCACACTTG-TATTTTCTG-3' (SEQ ID NO:10), F4: 5'-CAGGCAAC-CTCGGGAGGTAG-3' (SEQ ID NO:11), Sp6: 5'-ATTTAG-GTGACACTATAG-3' (SEQ ID NO:12). Primers used for checking the second round recombination events were F6: 5'-ATACAACATGGTGCCATTCTG-3' (SEQ ID NO:13) and R6: 5'-CTGGACTGGTGTGAGGCAGGTG-3' (SEQ ID NO:14); F7: 5'-ACACTCGCCAGACATAAAATC-3' (SEQ ID NO:15) and BAC-Sp6-R:5'-ACCGTTCAGCTGGATAT-TACGGC-3' (SEQ ID NO:16).

Results

The general strategy for generating the full length Tyrp-1 gene is shown in FIGS. 1A-D. The starting materials were two different BACs, both more than 100 kb in length. Tyrp-1

BAC1 contained the exons 1-8 of the Tyrp-1 gene, whilst Tyrp-1 BAC2 contained the upstream regulatory regions together with exons 1 and 2 of the Tyrp-1 gene. The BACs were sequenced using T7 and Sp6 universal primers to confirm the orientation and breakpoint of the Tyrp-1 gene. The method for generating the unified BAC containing the full length Tyrp-1 gene is best described by splitting into two steps: retrieval and recombination. Retrieval ($1^{st}$ round) consists of tagging the Tyrp-1 BAC1 with a selectable marker (frt-$Kan^R$-frt) and cloning of the $Kan^R$ tagged 22,463-bp DNA sequence into a retrieval vector, pBRBAC-AB. Recombination ($1^{st}$ round) consists of the site-specific insertion of this 22,463-bp DNA fragment (3,749-bp frt-$Kan^R$-frt cassette+18,714-bp Tyrp-1 genomic DNA containing a 2,950-bp overlap with Tyrp-1 BAC2) into Tyrp-1 BAC2 followed by the removal of the $Kan^R$ gene to generate the unified Tyrp-1 BAC. The retrieval-recombination process was then repeated to insert a 19,891-bp DNA fragment (1,896-bp loxP-$Kan^R$-loxP cassette +17,995-bp genomic DNA containing 3,320-bp overlap with the unified Tyrp-1 BAC) further downstream from the previous one. This fragment was retrieved and site-specifically inserted into the unified Tyrp-1 BAC to create the final product, the extended unified Tyrp-1 BAC that has 31,160-bp more Tyrp-1 genomic DNA than the original Tyrp-1 BAC2.

Retrieval

Figure 1B:
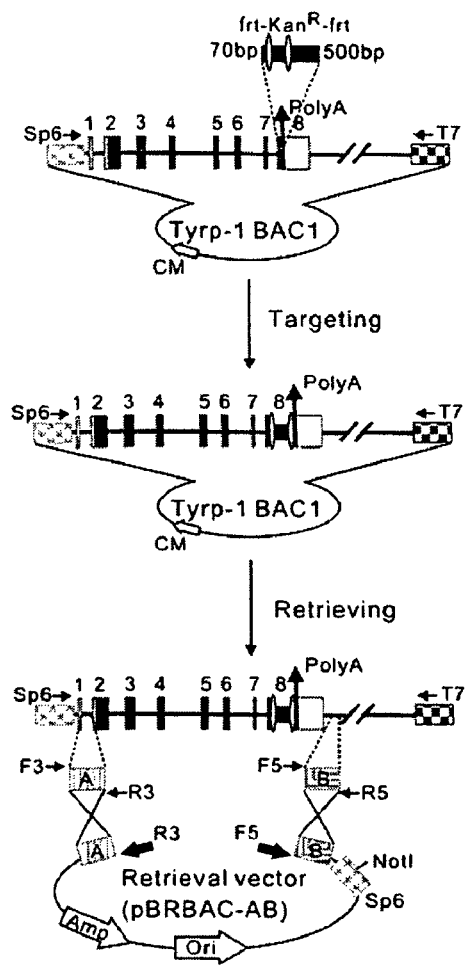

DNA engineering often requires the introduction of a selectable marker into a targeted gene in order to select the targeted candidate conveniently either in E. coli or in mammalian cells (13). Our initial task was to introduce a selectable marker into the targeted gene to facilitate later candidate identification. This would facilitate selection both during retrieval and later recombination into Tyrp-1 BAC2. As the BACs originally encoded Chloramphenicol resistance, a frt-$Kan^R$-frt cassette was introduced between the eighth exon and polyadenylation site. Red-mediated homologous recombination was facilitated by two regions (70-bp and 500-bp) of homology flanking the frt-$Kan^R$-frt cassette (FIG. 1B). Approximately 500 $Kan^R$ colonies were obtained from 42° C. treated cells, compared to 10 colonies from uninduced cells (Table 1).

TABLE 1

Efficiency of Homologous Recombination

| Step | [a]Number of Colonies obtained Non-induced | Induced | Number of colonies examined | Number of correct colonies | [b]Efficiency (%) | Length of Homology arms |
|---|---|---|---|---|---|---|
| Insertion of Kan | 10 | 500 | 22 | 14 | 64 | 70 bp 500 bp |
| Retrieval of the 22.5 kb DNA | 38 | 3600 | 28 | 26 | 93 | 216 bp 330 bp |
| BAC Recombination | 0 | 1500 | 11 | 10 | 90 | 216 bp 303 bp |
| Reported Retrieval (10) | — | 555 | 12 | 8 | 67 | 53 bp 51 bp |

[a]Induced DY380 competent cells carrying the modified BAC1 and BAC2 were electroporated with different linear DNA. The total number of colonies obtained is shown.
[b]Efficiency is defined as the number of correct recombinants as a percentage of the number of examined colonies.

Figure 2A:
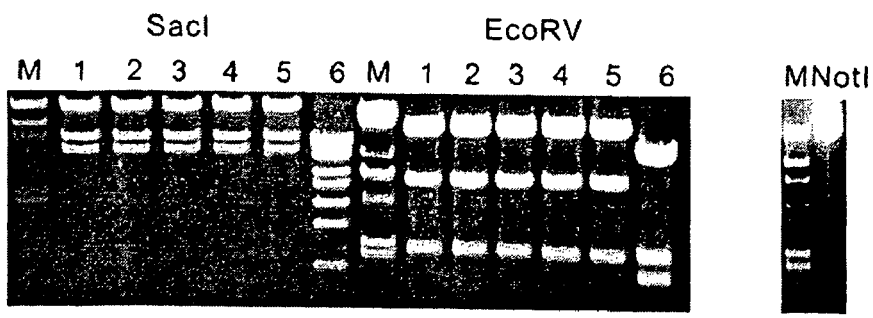

Homologous recombination was then used to retrieve the 22.5 kb sequence of interest from Tyrp-1 BAC1 containing the newly inserted frt-$Kan^R$-frt cassette, and then insert this fragment into a retrieval vector. pBR322 was used as the backbone of the retrieval vector due to its low copy number which had low toxicity to the bacterial strain when carrying a very large fragment (10). The retrieval vector contained an ampicillin resistance gene, an origin of replication, a Sp6 fragment to facilitate sequencing, and two homologous end sequences, one from the breakpoint of Tyrp-1 BAC1 and one from the region 4 kb downstream from the stop codon (encoding 216-bp and 330-bp of homology, respectively). A linearized vector was generated by PCR amplification using the R3 and F5 primers. This linearized retrieval vector was transformed into DY380 competent cells carrying Tyrp-1 BAC1, the transformants were then selected on LB-media plates containing both kanamycin and ampicillin. Homologous recombination generated a circular plasmid consisting of the 22.5 kb Tyrp-1 DNA cloned into pBRBAC-AB (FIG. 1B). In this step, some 3,600 $Kan^R$ colonies were obtained from red-induced cells compared to 38 colonies from uninduced cells (Table 1). 26 out of 28 clones examined were correct recombinants (93%). The data indicated that by using homology arms of more than 200-bp in length, a homologous recombination efficiency over 90% could be achieved. This compares to a previously reported 60% efficiency when homology arms of 50-bp in length were used to retrieve a 25 kb fragment from a BAC (10), (Table 1, supra). Representative results are shown in FIG. 2A, left panel. Digestion of six retrieved colonies with Sac I and EcoRV showed that only one had an abnormal digestion pattern (Expected digestion pattern for Sac I: 15,189-bp, 5,787-bp and 4,417-bp; for EcoRV :16,975-bp, 6,248-bp and 2,173-bp).

Recombination

Figure 1C:
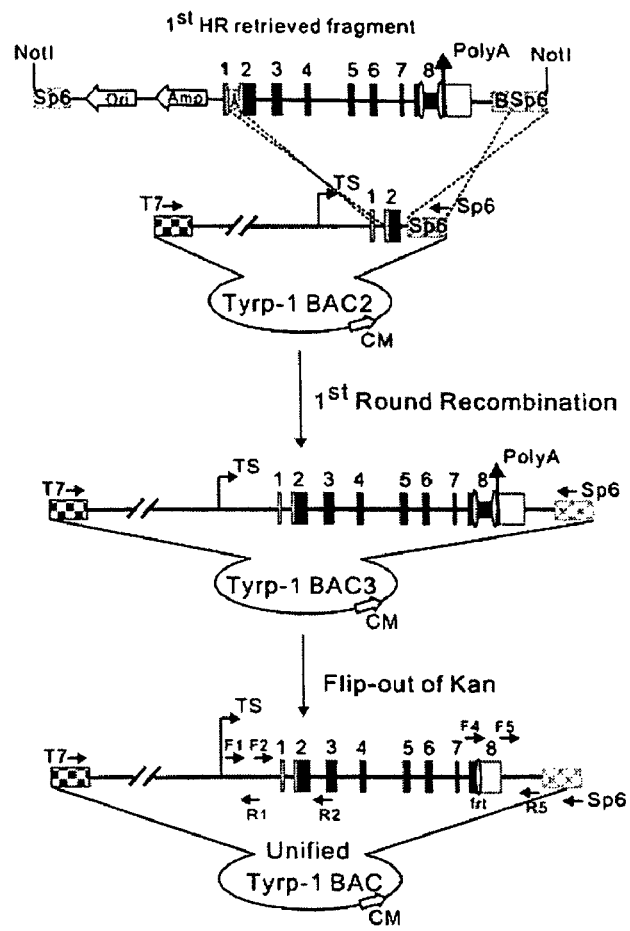
Figure 2B:
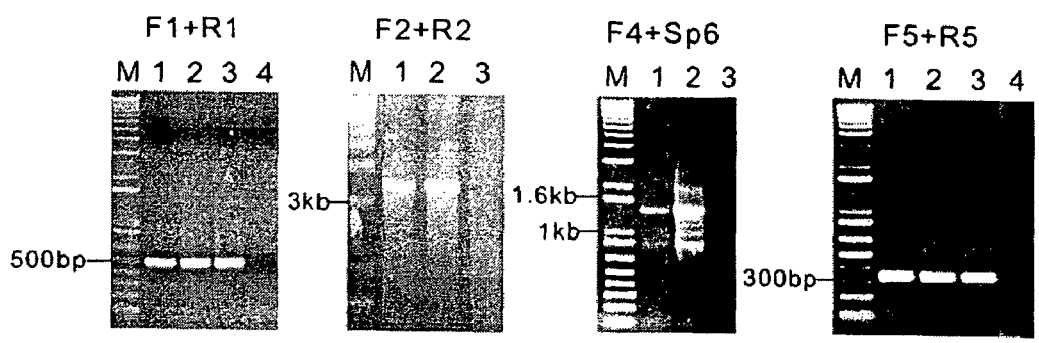
Figure 2C:
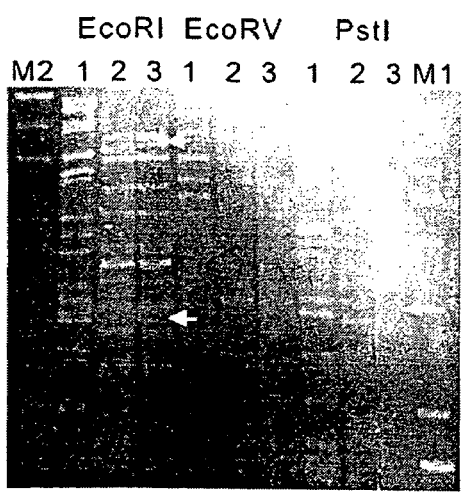

After the cloning of the 22.5 kb Tyrp-1 fragment, the pBRBAC-AB vector containing the retrieved fragment was linearized by NotI digestion (right panel, FIG. 2A) and transformed into DY380 cells containing Tyrp-1 BAC2. Homologous recombination occurred between the retrieved Tyrp-1 DNA and Tyrp-1 BAC2 through the 216-bp ArmA and the 303-bp Sp6 fragment to give rise to the Tyrp-1 BAC3 (FIG. 1C). Kanamycin and chloramphenicol double resistant colonies were selected. Over 1,500 $Km^R$+$Cm^R$ colonies were obtained from the induced cells; no colonies were obtained from uninduced cells (Table 1, supra). PCR amplification was used to determine whether the 22.5 kb Tyrp-1 DNA fragment was inserted precisely into Tyrp-1 BAC2. Several pairs of primers at different positions were used. Results from the PCR amplification showed that the recombination occurred as expected in 10 of 11 clones examined. A full length Tyrp-1 gene was obtained in Tyrp-1 BAC3 (FIG. 2B). Moreover, one of the recombinant BAC was further analyzed by DNA fingerprinting (FIG. 2C) and sequencing (data not shown). The data showed that the retrieved 22.5 kb DNA fragment had been precisely inserted into the Tyrp-1 BAC2 by homologous recombination. These data indicated that this targeting reaction was very efficient due to the longer homologous recombination arms between the targeting fragment and Tyrp-1 BAC2.

Although the selectable marker provides an easy method to select the targeted colonies, it might have interfered with Tyrp-1 gene expression (13) and with the next round of recombination. Selectable markers were therefore removed after targeting to eliminate any undesirable effects. Tyrp-1 BAC3 DNA was introduced into E. coli strain 294-Flp (12), which can express Flp recombinase to excise the kanamycin gene between the two frt sites, leaving only one frt site behind. This resulted in the unified Tyrp-1 BAC containing both the upstream regulatory elements and the eight coding exons.

Figure 1D:
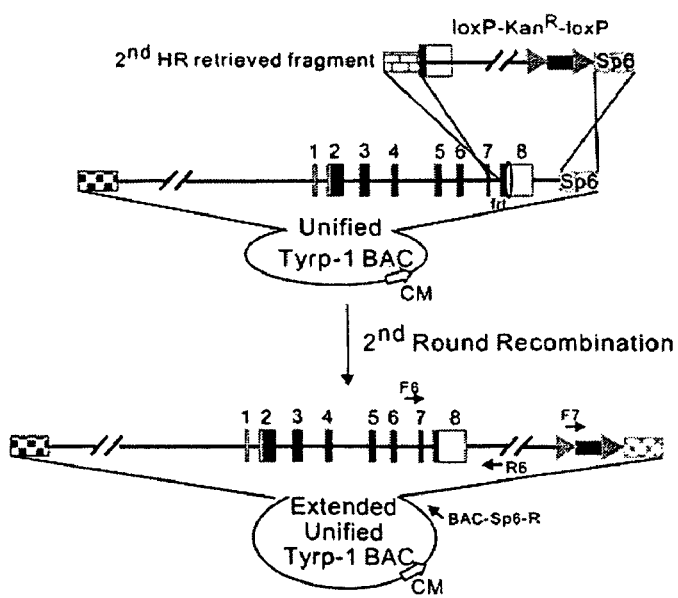
Figure 2D:
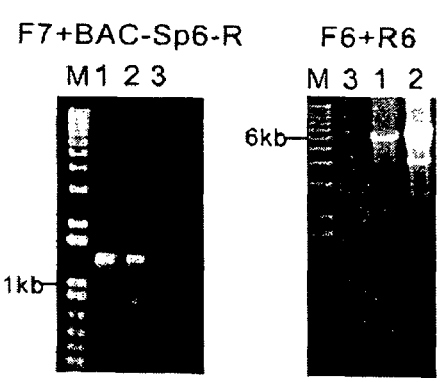
Figure 4:
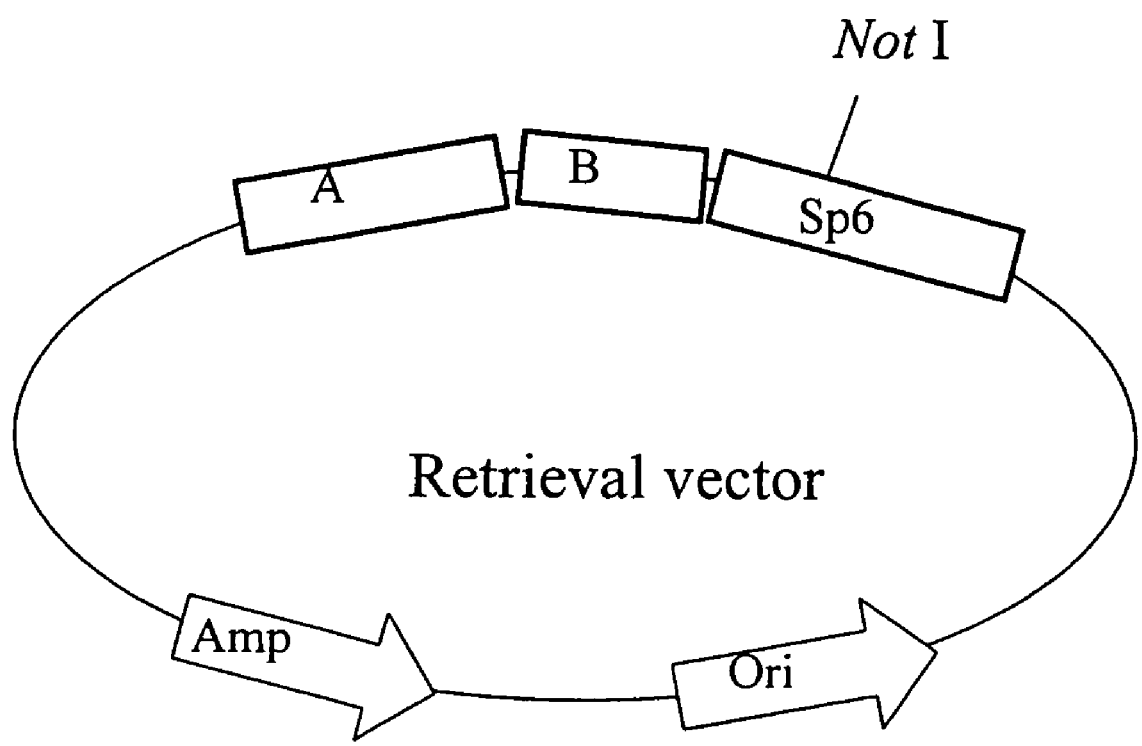

In order to further validate the approach, a second 19,891-bp DNA fragment was inserted into the unified BAC to precisely add sequence 3' to the coding region. A loxP-Kan$^R$-loxP cassette was inserted into the original Tyrp-1 BAC1 DNA at a position approximately 17-kb downstream of the poly(A) site to facilitate the retrieval. A second-round retrieval and recombination was carried out to generate the final product, the extended unified Tyrp-1 BAC (FIG. 1D). The recombination products were verified by PCR (FIG. 2D). Efficiency comparable to the first round of retrieval-recombination was obtained (data not shown).

Discussion

A unified Tyrp-1 BAC containing an intact gene has been generated by a two-step recombinogenic method. These results show that it is feasible to retrieve large DNA fragments from one BAC and precisely insert them into other BACs using Red-mediated homologous recombination. The design of the retrieval vector was the most important factor for subsequent homologous recombination. Insertion of the Sp6 fragment into pBR322 was vital as it incorporates the rare cutter NotI restriction site enabling later linearization of the retrieval plasmid, and provides a homologous arm for directional insertion of the retrieved DNA fragment into BACs. This data also indicates that longer homologous arms can generate more recombinant colonies as well as higher recombination efficiencies.

After removing the selectable marker in the Tyrp-1 BAC3 to generate the unified Tyrp-1 BAC, another round of retrieval-recombination can be carried out. The frt site left in Tyrp-1 BAC can be removed after the second round of recombination facilitated by a long homologous region upstream of the frt site (FIG. 1D). Through two rounds of retrieval-recombination, a total of 31,160-bp of genomic DNA from Tyrp-1 BAC1 was inserted into Tyrp-1 BAC2 in a site-specific manner. Since the loxP-Kan$^R$-LoxP sequence can be removed similarly to the frt-Kan$^R$-frt sequence, the approach described herein allows multiple rounds of retrieval-recombination, effectively enabling the construction of very large BACs limited only by the nature of the BAC backbone vector.

This method is not limited to BAC manipulation, it could be used to engineer any large DNA fragments or to insert large DNA fragments into the *E. coli* chromosome. With suitable vectors, this method may be used to construct and modify much larger DNA molecules such as Human Artificial Chromosomes (HAC). In this study, the templates for genomic DNA retrieval and recombination were BACs obtained through a library screen. However, it would be possible to avoid the library screen steps and generate these large DNA molecules by long range PCR or by direct recombinogenic retrieval from a complex genomic DNA mixture (14). Due to its simplicity, speed and precision, the method represents a powerful approach for BAC manipulation to aid in future studies of gene function in the post-genomic era.

The following references have been referred to throughout the specification. The entire content of these references is hereby incorporated by reference herein as background and illustrative of the state of the art of the invention.

REFERENCES

1. Copeland, N. G., Jenkins, N. A. and Court, D. L. (2001) Recombineering: a powerful new tool for mouse functional genomics. *Nature Rev. Genet.*, 2, 769-779.
2. Muyrers, J. P., Zhang, Y. and Stewart, A. F. (2001) Techniques: Recombinogenic engineering—new options for cloning and manipulating DNA. *Trends Biochem Sci*, 26, 325-331.
3. Cohen, S. N., Chang, A. C., Boyer, H. W. and Helling, R. B. (1973) Construction of biologically functional bacterial plasmids in vitro. *Proc Natl Acad Sci USA*, 70, 3240-3244.
4. Shizuya, H., Birren, B., Kim, U. J., Mancino, V., Slepak, T., Tachiiri, Y. and Simon, M. (1992) Cloning and stable maintenance of 300-kilobase-pair fragments of human DNA in *Escherichia coli* using an F-factor-based vector. *Proc Natl Acad Sci USA*, 89, 8794-8797.
5. Zhang, Y., Buchholz, F., Muyrers, J. P. P. and Stewart, A. F. (1998) A new logic for DNA engineering using recombination in *Escherichia coli*. *Nature Genet.*, 20, 123-128.
6. Yu, D., Ellis, H. M., Lee, E. C., Jenkins, N. A., Copeland, N. G. and Court, D. L. (2000) An efficient recombination system for chromosome engineering in *Escherichia coli*. *Proc. Natl Acad. Sci. USA*, 97, 5978-5983.
7. Datsenko, K. A. and Wanner, B. L. (2000) One-step inactivation of chromosomal genes in *Escherichia coli* K-12 using PCR products. *Proc. Natl Acad. Sci. USA*, 97, 6640-6645.
8. Muyrers, J. P., Zhang, Y., Benes, V., Testa, G., Ansorge, W. and Stewart, A. F. (2000) Point mutation of bacterial artificial chromosomes by ET recombination. *EMBO Rep*, 1, 239-243.
9. Muyrers, J. P., Zhang, Y., Testa, G. and Stewart, A. F. (1999) Rapid modification of bacterial artificial chromosomes by ET-recombination. *Nucleic Acids Res*, 27, 1555-1557.
10. Lee, E. C., Yu, D., Martinez de Velasco, J., Tessarollo, L., Swing, D. A., Court, D. L., Jenkins, N. A. and Copeland, N. G. (2001) A highly efficient *Escherichia coli*-based chromosome engineering system adapted for recombinogenic targeting and subcloning of BAC DNA. *Genomics*, 73, 56-65.
11. Jackson, I. J., Chambers, D. M., Budd, P. S. and Johnson, R. (1991) The tyrosinase-related protein-1 gene has a structure and promoter sequence very different from tyrosinase. *Nucleic Acids Res*, 19, 3799-3804.
12. Buchholz, F., Angrand, P. O. and Stewart, A. F. (1996) A simple assay to determine the functionality of Cre or FLP recombination targets in genomic manipulation constructs. *Nucleic Acids Res*, 24, 3118-3119.
13. Lewandoski, M. (2001) Conditional control of gene expression in the mouse. *Nat Rev Genet*, 2, 743-755.
14. Zhang, Y., Muyrers, J. P., Testa, G. and Stewart, A. F. (2000) DNA cloning by homologous recombination in *Escherichia coli*. *Nat Biotechnol*, 18, 1314-1317.

We claim:

1. A method of red mediated bacterial artificial chromosomal construction of DNA sequences in excess of about 20 kb, comprising the steps of:
   a.) providing a first DNA sequence or segment in excess of about 20 kB;
   b.) adding a first selectable marker cassette flanked by a recombination sequence on a first end of the first DNA segment or sequence;
   c.) adding an Sp6 element containing a NotI cutting site at the first end to form a first insert;
   d.) providing a linearized bacterial artificial chromosome retrieval vector that has an origin of replication and a second selectable marker different from the first insert, and that has homologous arms longer than about 200 base pairs that correspond to the first insert on either end thereof;
   e.) inserting the first insert and retrieval vector into a DY380 cell under conditions that enable the DY380 cell to effect homologous recombination between inserted DNA molecules;
   f.) selecting the recombined insert-vector molecules using first and second selectable markers;
   g.) linearizing the complex of recombined molecules using the NotI site in Sp6 fragment;
   h.) identifying and isolating a second DNA segment for combination with the first DNA segment that has an overlapping homology region of at least 200 base pairs with the first DNA segment on one end;
   i.) cloning the second DNA segment into a second retrieval vector that has a selectable marker different from both the cassette used in the first DNA insert and the selectable marker in the first retrieval vector, and an Sp6 fragment with a NotI cutting site;
   j.) inserting the linearized complex from step (g) with the second DNA segment-vector complex into a DY380 cell, and allowing the DY380 cell to effect a homologous recombination event between the two inserted molecules;
   l.) selecting the recombined insert-vector molecules utilizing the selectable marker from the first insert and the selectable marker from the second retrieval vector; and
   m.) transferring the isolated DNA from step (j) into a cell line that mediates the site-specific recombination mechanism indicated by flanking sites selected in step (b), to remove the selection cassette from the first insert, thereby forming a vector-insert construct containing a contiguous segment of DNA equal to or larger than about 40 kb.

2. The method of claim 1, additionally comprising the steps of:
   n.) providing a third DNA segment that is to be combined with the first and second DNA segments, the third DNA segment having an overlapping homology region of at least 200 base pairs with the second DNA segment on one terminus;
   o.) adding a selectable marker cassette flanked by site specific recombination sequences on a first end with the homology region to a third DNA segment or sequence;
   p.) adding a Sp6 element containing a NotI cutting site at the first end to form a third DNA Insert;
   q.) cutting the product of step (p) with NotI to obtain a linearized third DNA insert that has homologous arms that correspond to the first insert for longer than 200 base pairs on either end;
   r.) inserting the third insert and the linearized vector from step (n) into a DY380 cell under conditions that enable the DY380 cell to effect a homologous recombination event between the inserted molecules;

s.) selecting the recombined insert-vector molecules utilizing both selectable markers; and t.) transferring the isolated DNA from step (s) into a cell that mediates the recombination mechanism chosen to flank the selection, thereby forming a vector-insert construct containing a contiguous segment of DNA that spans the first, second, and third segments.

3. The method of claim 1, where the cell expresses Red α/β protein and/or Rec E/T protein from a construct which is stably integrated into the cell line.

4. The method of claim 1, wherein the recognition sequence is LoxP or frt.

* * * * *

SEQUENCE LISTING

<160> NUMBER OF SEQ ID NOS: 16

<210> SEQ ID NO 1
<211> LENGTH: 31

-continued

```
<212> TYPE: DNA
<213> ORGANISM: Artificial Sequence
<220> FEATURE:
<223> OTHER INFORMATION: Primer

<400> SEQUENCE: 1
tttgtcgacg ctgttcgaag ccttcacaac c                          31

<210> SEQ ID NO 2
<211> LENGTH: 31
<212> TYPE: DNA
<213> ORGANISM: Artificial Sequence
<220> FEATURE:
<223> OTHER INFORMATION: Primer

<400> SEQUENCE: 2
tttgagctcc atgtgtggca aggactgtga c                          31

<210> SEQ ID NO 3
<211> LENGTH: 27
<212> TYPE: DNA
<213> ORGANISM: Artificial Sequence
<220> FEATURE:
<223> OTHER INFORMATION: Primer

<400> SEQUENCE: 3
ttcatatggc aaaatctctt cagcgtc                               27

<210> SEQ ID NO 4
<211> LENGTH: 28
<212> TYPE: DNA
<213> ORGANISM: Artificial Sequence
<220> FEATURE:
<223> OTHER INFORMATION: Primer

<400> SEQUENCE: 4
ttgatatcga agagattttc tgccagac                              28

<210> SEQ ID NO 5
<211> LENGTH: 27
<212> TYPE: DNA
<213> ORGANISM: Artificial Sequence
<220> FEATURE:
<223> OTHER INFORMATION: Primer

<400> SEQUENCE: 5
tgatatctca tttcatgcca gtgccac                               27

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
gagctcagaa caaataaaac c                                     21

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
```

-continued tctagactttt tctgttttaat gtt                                              23

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
taagtaggct tcagtgacta gattc                                              25

<210> SEQ ID NO 9
<211> LENGTH: 25
<212> TYPE: DNA
<213> ORGANISM: Artificial Sequence
<220> FEATURE:
<223> OTHER INFORMATION: Primer

<400> SEQUENCE: 9
gcctcacgat aacaattccc tctac                                              25

<210> SEQ ID NO 10
<211> LENGTH: 26
<212> TYPE: DNA
<213> ORGANISM: Artificial Sequence
<220> FEATURE:
<223> OTHER INFORMATION: Primer

<400> SEQUENCE: 10
ggccaatgtc acacttgtat tttctg                                             26

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
caggcaacct cgggaggtag                                                    20

<210> SEQ ID NO 12
<211> LENGTH: 18
<212> TYPE: DNA
<213> ORGANISM: Artificial Sequence
<220> FEATURE:
<223> OTHER INFORMATION: Primer

<400> SEQUENCE: 12
atttaggtga cactatag                                                      18

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
atacaacatg gtgccattct g                                                  21

<210> SEQ ID NO 14
<211> LENGTH: 22
<212> TYPE: DNA
<213> ORGANISM: Artificial Sequence -continued

```
<220> FEATURE:
<223> OTHER INFORMATION: Primer

<400> SEQUENCE: 14
ctggactggt gtgaggcagg tg                                                    22

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
acactcgcca gacataaaat c                                                     21

<210> SEQ ID NO 16
<211> LENGTH: 23
<212> TYPE: DNA
<213> ORGANISM: Artificial Sequence
<220> FEATURE:
<223> OTHER INFORMATION: Primer

<400> SEQUENCE: 16
accgttcagc tggatattac ggc                                                   23
```